United States Patent
Sugihara

(10) Patent No.: US 8,262,941 B2
(45) Date of Patent: Sep. 11, 2012

(54) REACTION ACCELERATOR FOR SYNTHESIZING A CONDUCTIVE POLYMER, A CONDUCTIVE POLYMER, AND A SOLID ELECTROLYTIC CAPACITOR

(75) Inventor: Ryousuke Sugihara, Osaka (JP)

(73) Assignee: Tayca Corporation, Osaka-shi (JP)

( * ) Notice: Subject to any disclaimer, the term of this patent is extended or adjusted under 35 U.S.C. 154(b) by 0 days.

(21) Appl. No.: 13/240,75

(22) Filed: Sep. 22, 2011

(65) Prior Publication Data

US 2012/0016156 A1    Jan. 19, 2012

Related U.S. Application Data

(62) Division of application No. 12/303,893, filed as application No. PCT/JP2007/060768 on May 28, 2007, now abandoned.

(30) Foreign Application Priority Data

Jun. 7, 2006    (JP) .................................. 2006-158238

(51) Int. Cl.
*H01B 1/00* (2006.01)
*C08G 75/00* (2006.01)
*C08G 73/06* (2006.01)

(52) U.S. Cl. ......... 252/500; 528/377; 528/422; 528/423

(58) Field of Classification Search .................. 252/500; 528/377, 422, 423
See application file for complete search history.

(56) References Cited

U.S. PATENT DOCUMENTS

| 1,701,259 | A | 2/1929 | Crossley et al. |
| 5,182,347 | A | 1/1993 | Gerber |
| 6,344,966 | B1 | 2/2002 | Monden et al. |
| 2006/0223976 | A1 | 10/2006 | Tozawa et al. |

FOREIGN PATENT DOCUMENTS

| EP | 1661931 A1 | 5/2006 |
| JP | 10-050558 A | 2/1998 |
| JP | 2000-106331 A | 4/2000 |
| JP | 2003-158043 A | 5/2003 |
| JP | 2003-160647 A | 6/2003 |
| JP | 2003-226743 A | 8/2003 |
| JP | 2004-349525 A | 12/2004 |
| JP | 2005-154481 A | 6/2005 |
| JP | 2007-119633 A | 5/2007 |
| WO | 2005-014692 A1 | 2/2005 |
| WO | 2006-085601 A1 | 8/2006 |

OTHER PUBLICATIONS

International Search Report of PCT/JP2007/060768, mailing dated of Aug. 14, 2007.
Supplementary European Search Report dated Mar. 5, 2010, issued in corresponding European Patent Application No. 07744202.8.

*Primary Examiner* — Mark Kopec
*Assistant Examiner* — Jaison Thomas
(74) *Attorney, Agent, or Firm* — Westerman, Hattori, Daniels & Adrian, LLP

(57) ABSTRACT

There is provided a reaction accelerator for polymerizing a conductive polymer, comprising: a salt of an anion derived from a sulfonic acid having a skeleton of benzene or naphthalene having at least one OH group, and at least one divalent or more cation other than a transition metal cation. There is also provided a conductive polymer including the salt concerning the reaction accelerator. There is also provided a solid electrolyte capacitor including the conductive polymer as a solid electrolyte. The conductive polymer has a high electric conductivity and good heat-resistance. The solid electrolyte capacitor is reliable for an extended period of time.

6 Claims, No Drawings

REACTION ACCELERATOR FOR SYNTHESIZING A CONDUCTIVE POLYMER, A CONDUCTIVE POLYMER, AND A SOLID ELECTROLYTIC CAPACITOR

CROSS-REFERENCE TO RELATED APPLICATIONS

This Application is a Division of U.S. application Ser. No. 12/303,893 filed Dec. 8, 2008, which is a national stage of International Application No. PCT/JP2007/060768 filed May 28, 2007, which is based upon and claims the benefit of priority from the prior Japanese Patent Application No. 2006-158238 filed Jun. 7, 2006, the entire contents of which are incorporated herein by reference.

TECHNICAL FIELD

The present invention relates to a reaction accelerator used for synthesizing a conductive polymer, a conductive polymer produced by using the reaction accelerator, and a solid electrolytic capacitor including the conductive polymer as a solid electrolyte.

BACKGROUND ART

The solid electrolytic capacitor using the conductive polymer as a solid electrolyte is less likely to ignite and has a low ESR (equivalent series resistance), compared with conventional solid electrolytic capacitors using manganese dioxide, a solid electrolyte. Thus, in view of various excellent characteristics, the market has been expanded rapidly.

The conductive polymer as mentioned above is generally manufactured by a chemical oxidative polymerization method. For example, a transition metal salt of an organic sulfonic acid such as iron p-toluenesulfonate is used as an oxidizer dopant solution, and a monomer such as thiophene or its derivative is polymerized. See patent publications Nos. 1 and 2 identified below.

Although this method was fit for mass production application, there was a problem that the transition metal used as an oxidizer could remain in the conductive polymer. Even if a washing process is performed in order to remove the transition metal, the transition metal is one having a character which is difficult to be removed completely. Thus, there was a request to improve the stability of a conductive polymer and a long-term reliability of a solid electrolytic capacitor by removing the influences of the transition metal on the conductive polymer or on the solid electrolyte capacitor in case where the transition metal remains in the conductive polymer. Therefore, there was a proposal to use an oxidizer made of one other than transition metal salts; i.e., peroxides, for example. However, there was still a problem that compared with the transition metal salts, the reactivity or the electric conductivity of the obtained conductive polymer was significantly low.

[Patent document 1]: Japanese Laid Open Patent Publication No. 10-50558, and [Patent document 2]: Japanese Laid Open Patent Publication 2000-106331.

DISCLOSURE OF THE INVENTION

Objective of the Invention

The present invention has been accomplished in view of the above problems of the conventional technology. It promotes the synthetic reaction of a conductive polymer. There is provided a reaction accelerator for preparing a conductive polymer while incorporating it into the obtained conductive polymer, thereby improving the electric conductivity of the conductive polymer. There is also provided a conductive polymer obtained by using the reaction accelerator. There is further provided a solid electrolytic capacitor including the conductive polymer as a solid electrolyte, which is reliable over a long period of time.

Means for Solving the Objective

The inventors of the present invention have researched in order to solve the objectives and found a reaction accelerator for preparing a conductive polymer. The reaction accelerator includes a salt of an anion derived from a sulfonic acid having a skeleton of benzene or naphthalene having at least one OH group, and at least one divalent or more cation other than a transition metal cation. Using the reaction accelerator, a conductive polymer is polymerized. It promotes the polymerization reaction of the monomers for the conductive polymer, thereby resulting in efficient production of a conductive polymer with a good electric conductivity. Also, the conductive polymer is used as a solid electrolyte to obtain a solid electrolytic capacitor which is reliable over a long period of time.

As stated above, the reaction accelerator for the conductive polymer composition of the present invention is characterized in that it includes a salt of an anion derived from a sulfonic acid having a skeleton of benzene or naphthalene having at least one OH group, and at least one divalent or more cation other than a transition metal cation.

Also, the conductive polymer of the present invention is characterized in that it includes a salt of an anion derived from a sulfonic acid having a skeleton of benzene or naphthalene having at least one OH group, and at least one divalent or more cation other than a transition metal cation in a matrix of the conductive polymer.

Furthermore, the solid electrolytic capacitor of the present invention is characterized in that it includes the conductive polymer of the present invention as a solid electrolyte.

Effect of Invention

According to the present invention, there is provided a reaction accelerator in which the polymerization reaction of the monomer can be promoted in the process of preparing a conductive polymer. The electric conductivity of the conductive polymer can be maintained high. The solid electrolytic capacitor can be reliable over a long period of time.

Namely, according to the present invention, a specific salt is used as a reaction accelerator for obtaining a conductive polymer. The reaction accelerator does not include a transition metal (transition metal cation) which causes acceleration of the degradation of the conductive polymer. The salt concerned in the reaction accelerator is incorporated into the conductive polymer, thereby improving the electric conductivity, while efficiently polymerizing monomers. As results, a conductive polymer can be produced, which has a electric conductivity and an excellent heat resistance. Moreover, when using the conductive polymer as a solid electrolyte, there is provided a solid electrolytic capacitor reliable over a long period of time compared with conventional ones.

The conductive polymer of the present invention has a high electric conductivity and does not include a transition metal salt. Thus, a rapid degradation caused by the transition metal salt does not occur in the present invention, though it was observed in conventional conductive polymers. Therefore, it can be mainly used as a solid electrolyte of a solid electrolytic capacitor. Other than that, it can be also used as e.g., a cathode active material for batteries, an electrification prevention sheet, an electrification prevention paint, an electrification prevention agent such as an electrification prevention resin, and a corrosive proof agent such as a corrosion proof paint, in light of the advantageous properties.

PREFERRED EMBODIMENTS OF THE INVENTION

The reaction accelerator for polymerizing a conductive polymer of the present invention (referred to as "reaction accelerator" hereafter) includes a salt of an anion derived from a sulfonic acid having a skeleton of benzene or naphthalene having at least one OH group, and at least one divalent or more cation (other than a transition metal cation).

The anion derived from a sulfonic acid having a skeleton of benzene having at least one OH group is an anion in which "H" (hydrogen) of a sulfonate group of a sulfonic acid having a skeleton of benzene having at least one OH group is eliminated. The anion derived from a sulfonic acid having a skeleton of naphthalene having at least one OH group is an anion in which "H" (hydrogen) of a sulfonate group of a sulfonic acid having a skeleton of naphthalene having at least one OH group is eliminated.

The anion derived from a sulfonic acid having a benzene or naphthalene skelton having at least one OH group can include ones derived from acids selected from the group consisting of phenol sulfonic acid, phenol disulfonic acid, cresol sulfonic acid, catechol sulfonic acid, dodecyl phenol sulfonic acid, sulfosalicylic acid, naphthol sulfonic acid, naphthol disulfonic acid, and naphthol trisulfonic acid. Among them, an anion derived from phenol sulfonic acid or an anion derived from cresol sulfonic acid can be used in particular.

The salt of the reaction accelerator of the present invention includes the anion as stated above and at least one divalent or more cation (other than a transition metal cation). The divalent or more cation is one which is divalent or more, including various inorganic cations and organic cations other than transition metals. The above-mentioned inorganic cation can include magnesium ion ($Mg^{2+}$), calcium ion ($Ca^{2+}$), strontium ion ($Sr^{2+}$), barium ion ($Ba^{2+}$), radium ion ($Ra^{2+}$), aluminum ion ($Al^{3+}$), etc. In particular, calcium ion, strontium ion, barium ion and aluminum ion can be used. Also, the organic cation can include e.g., ethylenediamine ion ($^+H_3NCH_2CH_2NH_3{}^+$), 1,3-propyldiamine ion ($^+H_3NCH_2CH_2CH_2NH_3{}^+$), and 1,2-propyldiamine ion [$^+H_3NCH_2CH(NH_3{}^+)CH_3$]. In particular, ethylenediamine ion can be used.

The salt of the reaction accelerator is composed of the anion and the cation. There is no specific limitation of the combination of the anion and the cation. The reaction accelerator can include a single salt, or a combination of two or more salts. Among the salts, phenolsulfonates such as calcium phenolsulfonate, strontium phenolsulfonate, barium phenolsulfonate, aluminum phenolsulfonate, ethylenediamine phenolsulfonate; and cresolsulfonates such as calcium cresolsulfonate, strontium cresolsulfonate, barium cresolsulfonate, aluminum cresolsulfonate, ethylenediamine cresolsulfonate can be particularly used.

The reaction accelerator of the present invention can be in particular in a form of an aqueous solution in which the above-mentioned salt dissolves in water. Moreover, in order to improve permeability, a small amount of an alcohol or a surface active agent can be added. In addition, the concentration of the above-mentioned salt can be 0.1 mol/l or more, or in particular, 0.5 mol/l or more, in case of a solution of the reaction accelerator. While mentioned later in detail, when preparing a conductive polymer using the reaction accelerator of the present invention, the above-mentioned salt regarding the reaction accelerator is in advance applied to the surface of a base material (capacitor element etc.) in order to form a conductive polymer. Alternatively, it can be applied to the base material to which a monomer and/or oxidizer have been applied. For example, a base material (or a base material to which a monomer and/or an oxidizer has been applied) can be immersed into the reaction accelerator in the form of a solution. In that case, when the reaction accelerator of the present invention is provided in a solution having the above-mentioned concentration, the operation as described above can apply the salt in a sufficient quantity, thereby improving the productivity of the conductive polymer. In addition, the upper limit of the concentration of the salt in the solution can be usually about 1 mol/l in view of the solubility of the salt.

The method for preparing the salt is not particularly limited. For example, an aqueous solution including a sulfonic acid having a benzene or naphthalene skeleton having at least one OH group can be neutralized with an alkali including a divalent or more cation other than a transition metal cation and an anion. Using such a process, a reaction accelerator can be prepared directly in the form of an aqueous solution. Also, as described in the Examples later, the reaction accelerator obtained as an aqueous solution form by the process above can be subjected to a process such as spray dry so as to isolate the salt, which can be then dissolved in water again to form a reaction accelerator solution in the form of an aqueous solution. According to this process, the concentration of the salt in the aqueous solution of the reaction accelerator can be more accurately adjusted.

The reaction accelerator in a state of an aqueous solution at a concentration of 5 mass % can be in a condition with a pH value of 1 or more, and in particular, of 4 or more. When the reaction accelerator is an aqueous solution having a pH value as explained above at the concentration of 5 mass %, it can be particularly used in the production of a conductive polymer for aluminum solid electrolytic capacitors. Also, the reaction accelerator in a state of an aqueous solution at a concentration of 5 mass % can be in a condition of a pH of 10 or less, or in particular, of 8 or less. Thus, when producing the salt for the reaction accelerator by means of the neutralization method as above-mentioned, the amounts of the acid and alkali added can be adjusted in order to meet the pH value of the aqueous solution of the obtained salts at the concentration of 5 mass %.

As to the salt concerning the reaction accelerator of the present invention, the anion of the salt is required to have at least one OH group. This is because OH group is considered to promote the polymerization reaction of the monomers as well as contribute the improvement of the conductivity of the obtained conductive polymer. The reason is not be proved, but it is considered that proton of the OH group promptly proceeds with the polymerization reaction and is made easy to be incorporated in the conductive polymer. Also, the reason why the anion of the salt is required to have a benzene or naphthalene skelton is because it can improve the heat resistance of the obtained conductive polymer when the salt is incorporated therein.

Although the reason is not proved, the polymerization reaction of monomers can be promoted and the heat resistance of the conductive polymer can be improved when using a divalent or more cation.

During polymerizing a conductive polymer, the reaction accelerator of the present invention can promote the polymerization reaction of the monomer, and can improve the productivity of the conductive polymer. Moreover, the salt for the reaction accelerator can be incorporated into the produced conductive polymer as acid form to be served as a dopant. If it remains in the conductive polymer as salt form, it can contribute to the improvement of the electric conductivity of the conductive polymer. Furthermore, the reaction accelerator of the present invention does not include a transition metal. Thus, it does not affect the conductive polymer. Rather, the salt is incorporated into a conductive polymer, thereby improving the heat resistance of the conductive polymer as explained above. Therefore, the conductive polymer obtained by using the reaction accelerator of the present invention become excellent in conductivity and heat resistance.

Namely, the conductive polymer of the present invention includes the salt regarding the reaction accelerator in the matrix of the conductive polymer. It can be particularly obtained by performing a chemical oxidation polymerization of monomers using the reaction accelerator and a persulfate as an oxidizer.

In the conductive polymer of the present invention, the conductive polymer serving as a matrix can be a polymer of at least one monomer selected from the group consisting of thiophene and its derivatives, pyrrole and its derivatives, and aniline and its derivatives.

The derivatives of thiophenes can include 3,4-ethylenedioxythiophene, 3-alkylthiophene, 3-alkoxythiophene, 3-alkyl-4-alkoxythiophene, 3,4-alkylthiophene, 3,4-alkoxythiophene. The derivatives of pyrroles can include 3,4-alkylpyrrole, and 3,4-alkoxypyrrole. Furthermore, the derivatives of anilines can include 2-alkylaniline, and 2-alkoxyaniline. The carbon number of the derivatives of the alkyl group or the alkoxy group in the derivatives of the thiophenes, the pyrroles and the anilines can be in particular 1 to 16.

Monomers in a liquid state can be used for polymerization as it is, but in order to advance the polymerization reaction more smoothly, the monomers can be diluted with an organic solvents such as methanol, ethanol, propanol, butanol, acetone, and acetonitrile, making it into a solution (an organic solution).

As a mode of the polymerization of the above-mentioned monomer, a different mode can be adopted depending on the type of application of the conductive polymer. For example, in a case where a conductive polymer is made in a shape such as a film to incorporate it into an application device of the conductive polymer, any mode can be adopted. In a case where a conductive polymer is used as a solid electrolyte of a solid electrolytic capacitor, the manufacturing process of the solid electrolytic capacitor can include the process in which the salt concerning the reaction accelerator can be directly applied on the surface of the capacitor element or in which the salt concerning the reaction accelerator can be applied after a monomer and/or an oxidizer has been applied in advance. Then, the monomer is polymerized on the surface of the capacitor element.

The example below is explained as to the polymerization process in order to form a conductive polymer directly on the capacitor element of a solid electrolytic capacitor. A conductive polymer is formed by carrying out Process (A), Process (B), Process (C), and Process (D).

Process (A) [Application process of a reaction accelerator]: A capacitor element is immersed in the reaction accelerator (which is usually in a form of a solution), or the reaction accelerator is applied on the capacitor element, thereby making the reaction accelerator permeate inside fine holes of the capacitor element. Then, the salt is dried to deposit on the surface of the capacitor element. The capacitor element can be immersed in the reaction accelerator for a period of 1 second to 5 minutes, for example. The capacitor element, which has been immersed or on which the reaction accelerator has been applied, can be dried at a condition of 20 to 100° C. for a period of 10 seconds to 10 minutes.

Process (B) (Application process of monomer): A monomer is diluted with an organic solvent to have a concentration of 5 to 100 mass %, and in particular, of 10 to 40 mass % to obtain a monomer solution. The capacitor element, having deposited salt on the surface in Process (A), is immersed for a period of 1 second to 5 minutes, for example.

Process (C) (application process of oxidizer): The capacitor element which is previously immersed into the monomer solution and taken out therefrom is immersed into an oxidizer solution for a period of 1 second to 5 minutes, for example, and then is taken out therefrom.

Process (D) (polymerization process): The capacitor element, on which the salt concerning a reaction accelerator, the monomer and the oxidizer are applied, is subjected to polymerization of the monomers at a temperature of 0 to 120° C., and in particular, 30 to 70° C., for a period of 1 minutes to 1 day, and in particular, 10 minutes to 2 hours.

Note that Process (A), Process (B), Process (C) and Process (D), respectively, can be carried out once to form a conductive polymer. However, note that each of these processes can be repeated several times to form a conductive polymer. Moreover, the order of Process (A), Process (B) and Process (C) can be changed arbitrarily.

For example, in a case where a film-shaped conductive polymer is formed, a base material of a ceramic board and a glass board can be used instead of a capacitor element. Other than that, the procedures similar to Process (A), Process (B), Process (C) and Process (D) can be performed to form a conductive polymer on the surface of the base material. Then, the conductive polymer can be removed from the base material.

The oxidizer for the oxidizer solution in Process (C) can be in particular persulfates, including sodium persulfate, barium persulfate, and organic persulfates (e.g., ammonium persulfate, alkylamine persulfate, and imidazole persulfate). Among them, organic persulfates can be especially used.

The alkylamine for the alkylamine persulfate can have an alkyl group having a carbon number of 1 to 12. Examples can include ones same as "alkylamine salt of a sulfonic acid having a benzene or naphthalene skeletone having at least one OH group and at least one sulfonate group" which are described later.

The imidazole salt constituting the imidazole persulfate can be imidazole per se or ones whose hydrogen atoms on the imidazole ring partially substituted with an alkyl group or phenyl group having a carbon number of 1 to 20. That is, the imidazole persulfate includes not only a salt of persulfate and imidazole but also a salt of persulfate and an imidazole derivative (e.g., an imidazole derivative in which some hydrogen atoms on the imidazole ring are substituted with an alkyl or phenyl group). The examples of persulfate imidazole (or imidazole derivatives) can include ones same as the "imidazole salt of a sulfonic acid having a benzene or naphthalene skeletone having at least one OH group and at least one sulfonate group" as mentioned later.

The persulfate can be usually used as a solution. The concentration of the persulfate in a solution can be more than 15 mass %, and in particular, more than 20 mass %. The upper limit of the persulfate concentration can be around 50 mass % in view of the solubility.

Also, in the process of preparing the conductive polymer, a solution of the following dopant for a conductive polymers can be used. The dopant solution for a conductive polymers is a solution dissolving at least one selected from the group consisting of alkylamine salts and imidazole salts of a sulfonic acid having a benzene or naphthalene skeletone having at least one OH group and at least one sulfonate group at a concentration of 40 mass % or more.

The above-mentioned dopant for conductive polymer, which is selected from the group consisting of alkylamine salts and imidazole salts of a sulfonic acid having a benzene or naphthalene skeletone having at least one OH group and at least one sulfonate group, is incorporated into a conductive polymer to serve as a dopant. Therefore, when a dopant solution for conductive polymer is used to produce a conductive polymer, the salt concerning the reaction accelerator serves as a dopant, as well as the salt in the dopant solution for conductive polymer is incorporated in the conductive polymer, thereby further improving the conductivity of the conductive polymer. Also, by using the dopant solution for conductive polymer, the polymerization reaction of a monomer can be further promoted.

Namely, the composition for polymerizing a conductive polymer including the reaction accelerator and the dopant solution for conductive polymer of the present invention can be separately packaged, for example. Using the composition to prepare a conductive polymer, the polymerization reaction of a monomer can be improved further, while producing a conductive polymer having an excellent electric conductivity.

When a conductive polymer is produced by using the above-mentioned dopant solution for conductive polymer, a persulfate as an oxidizer can be added into the dopant solution for conductive polymer to obtain an oxidizer dopant solution for conductive polymer. Thereby obtained oxidizer dopant solution for conductive polymer can be substituted for the oxidizer (persulfate) solution used in Process (C).

As the sulfonic acid having a benzene or naphthalene skeletone having at least one OH group and at least one sulfonate group, the following can be exemplified: e.g., phenol sulfonic acid, phenol disulfonic acid, cresol sulfonic acid, catechol sulfonic acid, dodecylphenol sulfonic, acid, sulfosalicylic acid, naphthol sulfonic, acid, naphthol disulfonic acid, and naphthol trisulfonic acid. The alkylamines constituting the alkylamine salts of the sulfonic acid having a benzene or naphthalene skeletone can include an alkyl group having a carbon number of 1 to 12. Examples thereof can be methylamine, ethylamine, propylamine, butylamine, octylamine, dodecylamine, 3-ethoxypropylamine, 3-(2-ethylhexyloxy) propylamine, etc.

Also, as the imidazole which constitutes imidazole salt of the sulfonic acid having a benzene or naphthalene skeletone, the following can be exemplified: imidazole per se and ones in which a part of hydrogen atoms on the imidazole ring is substituted with an alkyl group or phenyl group having a carbon number of 1 to 20. Namely, the term "imidazole salt of a sulfonic acid having a benzene or naphthalene skeletone having at least one OH group and at least one sulfonate group" can include a salt made of an imidazole and a sulfonic acid having a benzene or naphthalene skeletone having at least one OH group and at least one sulfonate group, as well as a salt made of an imidazole derivative and a sulfonic acid having a benzene or naphthalene skeletone having at least one OH group and at least one sulfonate group. The imidazole derivative can include ones in which a part of hydrogen atoms on the imidazole ring is substituted with an alkyl group or phenyl group.

Note that when the imidazole which constitutes imidazole salt of a sulfonic acid having a benzene or naphthalene skeletone is substituted with an alkyl group or phenyl group having a carbon number of 1 to 20, the second and fourth positions of the imidazole ring can be substituted in view of the production cost and good productivity.

Suitable examples of the imidazole to constitute the imidazole salt of a sulfonic acid having a benzene or naphthalene skeletone can include imidazole, 1-methylimidazole, 2-methylimidazole, 2-ethylimidazole, 2-butylimidazole, 2-undecylimidazole, 2-phenylimidazole, 4-methylimidazole, 4-undecylimidazole, 4-phenylimidazole, 2-ethyl-4-methylimidazole, and 1,2-dimethylimidazole. Among them, imidazole, 2-methylimidazole and 4-methylimidazole can be in particular used.

As a solvent of the above-mentioned dopant solution, it can be usually good with water, but an aqueous solution can be which includes an organic solvent with a water affinity, such as ethanol, at an concentration of around 50 volume % or less.

In case of an oxidizer dopant solution which is prepared by adding a persulfate into a dopant solution, as the concentration becomes higher, the synthetic reaction efficiency of the conductive polymer can be improved, thereby allowing synthesis of the conductive polymer having a higher electric conductivity. Therefore, as to at least one selected from the group consisting of alkylamine salts and imidazole salts of a sulfonic acid having a benzene or naphthalene skeletone having at least one OH group and at least one sulfonate group, the concentration of the dopant solution can be 40 mass % or more, and in particular, 70 mass % or more. When the dopant solution has a high concentration as such, the oxidizer dopant solution having a high concentration can be prepared. As to at least one selected from the group consisting of alkylamine salts and imidazole salts of a sulfonic acid having a benzene or naphthalene skeletone having at least one OH group and at least one sulfonate group, the upper limit of the concentration of the dopant solution can be 90 mass %.

The pH of the dopant solution can be 1 or more, and in particular, 4 or more. When producing a conductive polymer for an aluminum solid electrolyte capacitor, the pH of the oxidizer dopant solution can be 1 or more, thereby preventing the dissolution of the dielectric layer of the capacitor element pertaining to the aluminum solid electrolyte capacitor. By adjusting the pH of the dopant solution into 1 or more, there is provided an oxidizer dopant solution for preparing a conductive polymer used for an aluminum solid electrolyte capacitor. Also, the pH of the dopant solution can be 10 or less, and in particular, 8 or less.

Also, an emulsifier can be added into the dopant solution. The addition of the emulsifier can provide a solution serving as an oxidizer dopant which promotes the polymerization reaction of a monomer more uniformly. Although various kinds of emulsifiers can be used, alkylamine oxide can be especially used. The alkylamine oxide, even if remaining in the conductive polymer, does not remarkably reduce the electric conductivity of the conductive polymer. Also, when it is used as a solid electrolyte of a solid electrolyte capacitor, the alkylamine oxide does not remarkably reduce the function of the capacitor. The carbon number of the alkyl group of the alkylamine oxide can be 1 to 20. As the polymerization reaction of the monomer proceeds, the pH of the reaction system is decreased. The alkylamine oxide can prevent the decrease of the pH.

As mentioned above, into the dopant solution for a conductive polymer a persulfate can be further added to be used as an oxidizer dopant solution, which can be used for producing a conductive polymer. In that case, the concentration of the oxidizer dopant solution can affect the productivity of the conductive polymer, i.e., the reactivity at the time of polymerization of the monomer, resulting in affecting the manufacturing productivity and the characteristic, etc. Therefore, the concentration of the oxidizer dopant in the solution can be 25 mass % or more, and in particular, 30 mass % or more, and in more particular, 40 mass % or more, and yet in more particular, 55 mass % or more. Also, it can be 80 mass % or less.

Namely, if the concentration of the oxidizer dopant is too low, the effect by using the oxidizer dopant solution can be less expected. On the other hand, the concentration of more than 25 mass % can promote the polymerization reaction. The concentration of more than 30 mass % or more than 40 mass % can satisfy the manufacture efficiency and properties of the solid electrolyte capacitor (tantalum solid electrolyte capacitor, niobium solid electrolyte capacitor and aluminum solid electrolyte capacitor etc.), that is, the main application of the conductive polymer. The concentration of 55 mass % or more can bring further good results such as low ESR and high capacitance. However, if the concentration of the oxidizer dopant solution is higher than 80 mass %, the property can tend to decrease in turn. The concentration of the oxidizer dopant solution can be adjusted to be high as stated above. Use of such an oxidizer dopant solution and the reaction accelerator of the present invention will produce the conductive polymer, while improving the productivity of the conductive polymer as well as the manufacturing efficiency and properties of the solid electrolyte capacitor.

Moreover, the pH of the oxidizer dopant solution is important in case of aluminum solid electrolyte capacitor, in particular. If the pH is less than 1, the dielectric layer can be dissolved, harming the properties. The pH of the oxidizer dopant solution thus can be 1 or more, and in particular, 4 or more, but 10 or less, and in particular, 8 or less. Note that in case of producing a tantalum solid electrolyte capacitor, and a niobium solid electrolyte capacitor, etc., their dielectric layers are durable in acid resistance, so that the pH can be less than 1.

The pH of the reaction system becomes low as the polymerization reaction of the monomer progresses. However, when alkylamine oxide as mentioned above is added into the oxidizer dopant solution as an emulsifier (for example, when the oxidizer dopant solution is provided by using a dopant solution including the emulsifier), the alkylamine oxide can serve as preventing the decrease of the pH as well as proceeding with the polymerization reaction uniformly.

While the concentration of the oxidizer dopant solution is explained in view of production of a solid electrolyte capacitor, the concentration of the oxidizer dopant solution is also important when producing a conductive polymer. The concentration of the oxidizer dopant in the solution can be 25 mass % or more, and in particular, 30 mass % or more, and more in particular, 55 mass % or more. Also, it can be 80 mass % or less.

Also, the mixing ratio of a persulfate with an alkylamine salt or imidazole salt of a sulfonic acid having a benzene or naphthalene skeletone having at least one OH group and at least one sulfonate group in the oxidizer dopant solution can be as follows: Per 1 mole of the alkylamine salt or imidazole salt of a sulfonic acid having a benzene or naphthalene skeletone having at least one OH group and at least one sulfonate group, the persulfate can be added at 0.3 mol or more, and in particular, 0.4 mol or more, but 2.0 mol or less, and in particular, 1.5 mol or less. When the mixing ratio of the persulfate is more than the above range, the ratio of the alkylamine salt or imidazole salt of the specific organic sulfonic acid is decreased. As a result, the amount of the sulfuric acid ion as dopant is increased, thereby adversely affecting the improvement of the electric conductivity of the conductive polymer by the oxidizer dopant solution. On the contrary, the mixing ratio of the persulfate is less than the range as described above, it may become difficult to produce a conductive polymer.

As with the conductive polymer of the present invention obtained as mentioned above, the content of the cation derived from the salt regarding the reaction accelerator (that is, a divalent or more cation other than a transition metal cation) in the entire conductive polymer can be 10 ppm or more, and in particular, 20 ppm or more, and more in particular, 50 ppm or more. When the conductive polymer includes the divalent or more cation at the content stated above, better heat resistance can be obtained. Also, the upper limit of the divalent or more cation in the conductive polymer is not limited, but usually, it can be about 5000 ppm, and in particular, 1000 ppm, and more in particular, 500 ppm, and yet more in particular, 300 ppm or less. In view of balancing the advantageous effects by using the reaction accelerator (especially, the improvement of heat-resistant) and the economically disadvantageous effects by using a large amount of the reaction accelerator, the content of the divalent or more cation in the entire conductive polymer can be 10 ppm or more, and in particular, 20 ppm or more, and more in particular, 50 ppm or more, but 1000 ppm or less, and in particular, 500 ppm or less, and more in particular, 300 ppm or less. The content of the divalent or more cation in the conductive polymer can be measured by the method shown explained later.

The solid electrolyte capacitor of the present invention can use the conductive polymer of the present invention as a solid electrolyte. Other components can be similar to those used in conventional solid electrolyte capacitors. Various solid electrolyte capacitor can be prepared by selecting the material for the capacitor element such as aluminum solid electrolyte capacitor, niobium solid electrolyte capacitor and tantalum capacitor.

EXAMPLES

The present invention is described in detail hereafter based on examples. However, the following description of the examples does not restrict the present invention. Without departing from the scope inferred in the context, a modification is included in the present invention. In the following examples, the term "%" for the concentration of a solution, diluted solution, or dispersion solution, etc. means "mass %" unless otherwise stated.

First, synthesis examples of phenolsulfonate and cresolsulfonate are disclosed. They are used as a reaction accelerator in the examples.

Synthesis Example 1

Synthesis of Calcium Phenolsulfonate and Preparation of its Aqueous Solution

While 1000 g of a phenol sulfonic acid aqueous solution at a concentration of 5% was stirred at room temperature, calcium hydroxide was gradually added to reach a pH of about 6. The mixture was continuously stirred for a while. Then, this was filtered with 0.4 micrometer glass filter to obtain a calcium phenolsulfonate aqueous solution, which was then spray-dried to obtain powders of calcium phenolsulfonate.

Thereby obtained calcium phenolsulfonate is dissolved in pure water to become a concentration of 0.5 mol/l, which was then filtered with 0.2 micrometer filter to obtain an aqueous solution.

Synthesis Example 2

Synthesis of Strontium Phenolsulfonate, and Preparation of an Aqueous Solution Instead of using calcium hydroxide, strontium hydroxide was added in the same manner as Synthesis Example 1 so as to produce strontium phenolsulfonate. A solution thereof having a concentration of 0.5 mol/l was obtained.

Synthesis Example 3

Synthesis of Barium Phenolsulfonate, and Preparation of an Aqueous Solution

Instead of using calcium hydroxide, barium hydroxide was added in the same manner as Synthesis Example 1 so as to produce barium phenolsulfonate. A solution thereof having a concentration of 0.5 mol/l was obtained.

Synthesis Example 4

Synthesis of Calcium Cresolsulfonate, and Preparation of an Aqueous Solution Instead of using the phenol sulfonic acid solution, a cresol sulfonic acid solution was used in the same manner as Synthesis Example 1 so as to produce calcium cresolsulfonate. A solution thereof having a concentration of the 0.5 mol/l was obtained.

Synthesis Example 5

Synthesis of Ethylenediamine Phenolsulfonate, and Preparation of an Aqueous Solution Instead of using calcium hydroxide, ethylenediamine was added in the same manner as Synthesis Example 1 so as to produce ethylenediamine phenolsulfonate. A solution thereof having a concentration of 0.5 mol/l was obtained.

Synthesis Example 6

Synthesis of Ethylenediamine Sulfonate and Preparation of an Aqueous Solution of an Ethylenediamine Polystyrene Phenolsulfonate 1000 g of 5% phenol sulfonic acid solution was stirred at room temperature, while ethylenediamine was added slowly until the pH became about 6. The stirring was continued for a while. Then, this was filtered with 0.4 micrometer glass filter, so as to obtain an ethylenediamine phenolsulfonate solution, which was then spray-dried to obtain powders of ethylenediamine phenolsulfonate.

Then, 20% polystyrene sulfonic acid aqueous solution was stirred at room temperature while ethylenediamine was slowly added until a pH becomes about 5. Water was added to adjust a solution having a concentration of 20%. Into the mixture, the powders of the ethylenediamine phenolsulfonate were dissolved. Accordingly, a solution (pH 5), in which 0.5 mol/l of ethylenediamine phenolsulfonate was dissolved into 20% ethylenediamine polystyrene phenolsulfonate aqueous solution, was obtained.

Synthesis Example 7

Synthesis of Ethylenediamine Sulfonate and Preparation of a Solution of an Ethylenediamine Polystyrene Phenolsulfonate 1000 g of 5% phenol sulfonic acid solution was stirred at room temperature, while ethylenediamine was added slowly until the pH became about 1.5. The stirring was continued for a while. Then, this was filtered with 0.4 micrometer glass filter, so as to obtain an ethylenediamine phenolsulfonate solution, which was then spray-dried to obtain powders of ethylenediamine phenolsulfonate.

Then, 5% polystyrene sulfonic acid aqueous solution was stirred at room temperature while ethylenediamine was slowly added until a pH becomes about 1.5 and adjusted by distillation to a solution having a concentration of 20%. Into the solution, the powders of the ethylenediamine phenolsulfonate were dissolved. Accordingly, a solution (pH 1.5), in which 0.5 mol/l of ethylenediamine phenolsulfonate was dissolved into 20% ethylenediamine polystyrene phenolsulfonate aqueous solution, was obtained.

Synthesis Example 8

Synthesis of Aluminum Phenolsulfonate and an Aqueous Solution Thereof

Into 1000 g of 10% aluminum sulfate solution, 2N sodium hydroxide solution was added to adjust it into a pH of 7.6. The precipitates by this operation were collected by filtering them with 4 micrometer filter, and then dispersed into 1000 ml of pure water while stirring for 10 minutes. The precipitates were again collected by 4 micrometer filter. The process of the dispersion and the filtering was repeated three times. Then, the precipitates as collected was dispersed into 800 ml of pure water, into which 281 g of phenol sulfonic acid was added, while stirring it at room temperature for 15 hours. Then, the insoluble matter was removed with 0.4 micrometer filter, so as to obtain a solution of aluminum phenolsulfonate. By spray drying the solution, powders of aluminum phenolsulfonate was obtained.

Thereby obtained aluminum phenolsulfonate was dissolved in pure water such that its concentration became 0.5 mol/l, which was subject to 0.2 micrometer filter to obtain an aqueous solution.

Evaluation in Conductive Polymer

Example 1

A heat-resistant tape (2 mm in width) was stuck on a ceramic plate (40 mm in length and 3.3 mm in the width) in the transverse direction thereof such that the heat-resistant tape divides into a portion having 30 mm in size from one end of the lengthwise direction and another portion having a size of 10 mm from the other end of the lengthwise direction. Then, the portion having 30 mm in size extending from the one end of the lengthwise direction of the ceramic plate to the heat-resistant tape (29 mm×3.3 mm) was immersed into the 0.5 mol/l calcium phenolsulfonate solution (pH 6.0) prepared in Synthesis Example 1 for 1 minute. Then, the ceramic plate was taken out to place it into a drier at a temperature of 100° C. for 5 minutes. 35% ethanol solution of 3,4-ethylenedioxythiophene was prepared in advance, into which the portion of the ceramic plate where it was immersed into the calcium phenolsulfonate solution and dried in the drier was immersed at the depth of the heat-resistant tape for a period of 1 minute. Then, the ceramic plate was immersed into 45% ammonium persulfate aqueous solution for 10 seconds. A polymerization process was done for 40 minutes at room temperature to form a conductive polymer film. Then, the ceramic plate whose surface was partly covered with the conductive polymer film was immersed into pure water for 30 minutes, and it was taken out for drying it for 30 minutes at 70° C.

The series of the process from the step of immersing the ceramic plate into the calcium phenolsulfonate aqueous solution to the step of drying it at 70° C. for 30 minutes was repeated four times. Thereafter, the ceramic plate was dried at 150° C. for 60 minutes. Then, a load of 5 ton was applied for 5 minutes on the ceramic plate to equalize the thickness of the conductive polymer film.

Example 2

Instead of using the 0.5 mol/l calcium phenolsulfonate aqueous solution, the 0.5 mol/l strontium phenolsulfonate aqueous solution (pH 6.0) as prepared in Synthesis Example 2 was used. Other than that, the same procedures as Example 1 were performed so as to obtain a conductive polymer film formed on the surface of the ceramic plate.

Example 3

Instead of using the 0.5 mol/l calcium phenolsulfonate aqueous solution, the 0.5 mol/l aluminum phenolsulfonate aqueous solution (pH 6.0) as prepared in Synthesis Example 8 was used. Other than that, the same procedures as Example 1 were performed so as to obtain a conductive polymer film formed on the surface of the ceramic plate.

Example 4

Instead of using the 0.5 mol/l calcium phenolsulfonate aqueous solution, the 0.5 mol/l calcium cresolsulfonate aqueous solution (pH 6.0) as prepared in Synthesis Example 4 was used. Other than that, the same procedures as Example 1 were performed so as to obtain a conductive polymer film formed on the surface of the ceramic plate.

Example 5

Instead of using the 0.5 mol/l calcium phenolsulfonate aqueous solution, the 0.5 mol/l ethylenediamine phenolsulfonate aqueous solution (pH 5.0) as prepared in Synthesis Example 5 was used and the aqueous solution was kept at 60° C. Other than that, the same procedures as Example 1 were performed so as to obtain a conductive polymer film formed on the surface of the ceramic plate.

Example 6

Instead of using the 0.5 mol/l calcium phenolsulfonate aqueous solution, a solution (pH 5), in which 0.5 mol/l of ethylenediamine phenolsulfonate was dissolved into 20% ethylenediamine polystyrene phenolsulfonate aqueous solution as prepared in Synthesis Example 6, was used and the aqueous solution was kept at 60° C. Other than that, the same procedures as Example 1 were performed so as to obtain a conductive polymer film formed on the surface of the ceramic plate.

Example 7

Instead of using the 0.5 mol/l calcium phenolsulfonate aqueous solution, a solution (pH 1.5 when diluted into a concentration of 5%), in which 0.5 mol/l of ethylenediamine phenolsulfonate was dissolved into 20% ethylenediamine polystyrene phenolsulfonate aqueous solution as prepared in Synthesis Example 7, was used and the aqueous solution was kept at 60° C. Other than that, the same procedures as Example 1 were performed so as to obtain a conductive polymer film formed on the surface of the ceramic plate.

Example 8

Instead of using the 45% ammonium persulfate, an oxidizer dopant solution in which 40% ammonium persulfate was mixed with 70% 2-methylimidazole phenolsulfonate aqueous solution (pH 5.0) at a volume ratio of 1:1 was used. Other than that, the same procedures as Example 1 were performed so as to obtain a conductive polymer film formed on the surface of the ceramic plate.

Example 9

Instead of using the 45% ammonium persulfate, an oxidizer dopant solution in which 40% ammonium persulfate was mixed with 70% 2-methylimidazole phenolsulfonate aqueous solution (pH 5.0) at a volume ratio of 1:1 with further addition of decyldimethylamineoxide at a concentration of 0.2% was used. Other than that, the same procedures as Example 1 were performed so as to obtain a conductive polymer film formed on the surface of the ceramic plate.

Example 10

Instead of using the 45% ammonium persulfate, an oxidizer dopant solution in which 40% ammonium persulfate was mixed with 70% 4-methylimidazole phenolsulfonate aqueous solution (pH 5.0) at a volume ratio of 1:1 with further addition of decyldimethylamineoxide at a concentration of 0.2% was used. Other than that, the same procedures as Example 1 were performed so as to obtain a conductive polymer film formed on the surface of the ceramic plate.

Comparative Example 1

Instead of using 0.5 mol/l calcium phenolsulfonate aqueous solution, 0.5 mol/l sodium phenolsulfonate aqueous solution (pH 6.0) was used. Instead of repeating the polymerization process four times, the polymerization was repeated six times. Other than the differences, the same procedures as Example 1 were performed so as to obtain a conductive polymer film formed on the surface of the ceramic plate.

Comparative Example 2

Instead of using 0.5 mol/l calcium phenolsulfonate aqueous solution, 0.5 mol/l ammonium phenolsulfonate aqueous solution (pH 6.0) was used. Instead of repeating the polymerization process four times, the polymerization was repeated six times. Other than the differences, the same procedures as Example 1 were performed so as to obtain a conductive polymer film formed on the surface of the ceramic plate.

Comparative Example 3

Instead of using 0.5 mol/l calcium phenolsulfonate aqueous solution, 0.5 mol/l calcium m-xylenesulfonate aqueous solution (pH 6.0) was used. Instead of repeating the polymerization process four times, the polymerization was repeated six times. Other than the differences, the same procedures as Example 1 were performed so as to obtain a conductive polymer film formed on the surface of the ceramic plate.

Comparative Example 4

Instead of using 0.5 mol/l calcium phenolsulfonate aqueous solution, 0.5 mol/l sodium m-xylenesulfonate aqueous solution (pH 6.0) was used. Instead of repeating the polymerization process four times, the polymerization was repeated six times. Other than the differences, the same procedures as Example 1 were performed so as to obtain a conductive polymer film formed on the surface of the ceramic plate.

Comparative Example 5

Instead of using 0.5 mol/l calcium phenolsulfonate aqueous solution, 0.5 mol/l sodium butylnaphthalenesulfonate aqueous solution (pH 6.0) was used. Instead of repeating the polymerization process four times, the polymerization was repeated six times. Other than the differences, the same procedures as Example 1 were performed so as to obtain a conductive polymer film formed on the surface of the ceramic plate.

Comparative Example 6

40% butanol solution of ferric p-toluenesulfonate was mixed with 3,4-ethylenedioxythiophene at a mass ratio of 4:1, and the mixture was strongly shaken for 10 seconds. Into this mixture, the same ceramic plate as used in Example 1 was quickly immersed for 5 seconds, which was then taken out. The ceramic plate was kept for 30 minutes at room temperature and then it was immersed in pure water for 30 minutes. Then, the ceramic plate was taken out and dried for 30 minutes at 50° C.

The series of the process from the step of immersing the ceramic plate into the mixture of the ferric p-toluenesulfonate butanol solution and 3,4-ethylenedioxythiophene to the step of drying at 50° C. for 30 minutes was repeated five times to form a conductive polymer film on the surface of the ceramic plate. The subsequent procedures were the same as Example 1.

The electric conductivities of the conductive polymer films of Examples 1 to 10 and Comparative Examples 1 to 6 were measured in accordance with JIS K 7194 using a four probes electricity measurement instrument [MCP-T600 (brand name) by Mitsubishi Chemical Corporation]. The values obtained thereby are listed as "Initial Conductivity" in Table 1. The results in Table 1 were obtained by measuring the conductivity at five points of each conductive polymer film, from which an averaged value was calculated with rounding off the decimal points.

Also, after measuring the electric conductivity, the conductive polymer film on the ceramic plate was kept in a constant temperature bath at 150° C. for 100 hours, and then taken out. Then, the electric conductivity of the conductive polymer film was measured in the same way as described above. The results are listed in Table 1 as "Electric Conductivity after 100 Hour Storage at 150° C."

TABLE 1

|  | Initial Electric Conductivity (S/cm) | Electric Conductivity after 100 Hour Storage at 150° C. (S/cm) |
| --- | --- | --- |
| Example 1 | 68 | 45 |
| Example 2 | 66 | 43 |
| Example 3 | 62 | 40 |
| Example 4 | 59 | 40 |

TABLE 1-continued

|  | Initial Electric Conductivity (S/cm) | Electric Conductivity after 100 Hour Storage at 150° C. (S/cm) |
| --- | --- | --- |
| Example 5 | 70 | 47 |
| Example 6 | 71 | 48 |
| Example 7 | 78 | 49 |
| Example 8 | 75 | 55 |
| Example 9 | 87 | 64 |
| Example 10 | 88 | 66 |
| Comparative Example 1 | 57 | 21 |
| Comparative Example 2 | 56 | 19 |
| Comparative Example 3 | 41 | 1 |
| Comparative Example 4 | 38 | 0.9 |
| Comparative Example 5 | (*1) | (*1) |
| Comparative Example 6 | 60 | 1 |

Note that the mark (*1) in Table 1 indicates that a conductive polymer film on the surface of the ceramic plate was not obtained in a good condition so that its electric conductivity was not measured.

As understood from the results in Table 1, the conductive polymers of Examples 1 to 10 were more excellent in electric conductivity than those of Comparative Examples 3 and 4, and more excellent in heat resistance than those of Comparative Examples 1 to 6.

Note that in Comparative Examples 1 to 5, the polymerization process was repeated four times at first. However, since a conductive polymer was not formed on the given portion of the ceramic plate, the polymerization was further repeated two times. As results, a conductive polymer film was finally formed entirely at the given portions of the ceramic plate in Comparative Examples 1 to 4. However, a conductive polymer film still could not be formed in Comparative Example 5. On the contrary, fewer repetition of the polymerization process could form good conductive polymer films in Examples 1 to 10. The results show that the reactivity of 3,4-ethylenedioxy thiophene, a monomer, was promoted by the reaction accelerator containing a salt of an anion derived from phenol sulfonic acid or cresol sulfonic acid and a divalent or more cation other than a transition metal cation.

Moreover, the results in Example 1 and 8 to 10 using the same reaction accelerator, that is, calcium phenolsulfonate, are compared as follow: In Examples 8 to 10, instead of using an ammonium persulfate solution as an oxidizer solution, an oxidizer dopant solution including a conductive polymer polymerization dopant such as 2-methylimidazole phenolsulfonate or 4-methylimidazole phenolsulfonate was used. The conductive polymers in Examples 8-10 were better in characteristics than that in Example 1 in which 3,4-ethylenedioxythiophene was polymerized in an oxidizer solution without the dopant. The effects by using the reaction accelerator together with the oxidizer dopant solution including a dopant were proven. Further, in Examples 9 and 10, the dopant solution (or oxidizer dopant solution) containing decyldimethylaminooxide, an emulsifier was used. Compared with Example 8 not including such an emulsifier, the conductive polymers of Examples 9 and 10 were better in characteristics.

Next, the conductive polymer film of Example 1 was removed from the ceramic plate, 100 mg of which was put into a 50 ml vial with an airtight stopper. Then, 2 ml of sulfuric acid was added in it and kept at 50° C. for one day. Then, it diluted with water and was subjected to filtering. ICP measurement was performed to the solution. The amount of calcium ions in the conductive polymer was measured by using a calibration curve. It was measured as 103 ppm.

Also, the amount of ions in the conductive polymers of the conductive polymer films produced in accordance with Examples 2, 5, and 8 and Comparative Examples 1 and 3 was measured. Strontium ion was 68 ppm in Example 2; ethylenediamine ion was 60 ppm in Example 5; calcium ion was 65 ppm in Example 8; sodium ion was 4 ppm in Comparative Example 1; and calcium ion was 100 ppm in Comparative Examples 3. Furthermore, with respect to the conductive polymer film of Comparative Example 2, the same procedure as Example 1 was performed to prepare a solution to measure ammonium ion by ion chromatography, using the calibration curve. The concentration was 2 ppm.

The conductive polymer of Example 1 used calcium being a divalent cation, whereas the conductive polymer of Comparative Example 1 used sodium being a monovalent cation. Other than that, Example 1 was the same as Comparative Example 1. It is considered that the results listed in Table 1 show that the divalent or more cation as a reaction accelerator contributed has furthered improvement of the heat-resistant of the conductive polymer.

Also, the conductive polymer of Example 1 was different from that of Comparative Example 3 only in the anions concerning the reaction accelerators. It is considered that the results listed in Table 1 show that the anion concerning the reaction accelerator, derived from a sulfonic acid having a benzene skeleton containing at least one OH group, contributed to improve the initial characteristic (initial electric conductivity) and the heat-resistant (electric conductivity after storage) of the conductive polymer.

Evaluation Using an Aluminum Solid Electrolyte Capacitor

Example 11

An aluminum etched foil having a size of 10 mm in length and 3.3 mm in width was provided. A polyimide solution was applied to the transverse direction of the above-mentioned foil to have a width of 1 mm in such a way that a portion with 4 mm in size extended from one end of the lengthwise direction was divided from another portion with 5 mm in size extended from the other end. Then, the foil was dried. Then, a silver wire was attached as a positive electrode at the portion to have a size of 2 mm spaced from the end, which is located in said portion with 5 mm in size from the other end. The portion with 4 mm in size from one end of the lengthwise direction (4 mm×33 mm) was immersed into 10% adipic acid ammonium aqueous solution, while applying a voltage of 13V for chemical conversion treatment to form a dielectric coating so as to produce a capacitor element.

Next, into the 0.5 mol/l calcium phenolsulfonate aqueous solution (pH 6.0) prepared in accordance with Synthesis Example 1, the portion in which the dielectric coating was formed was immersed at the depth of the portion where the polyimide solution was applied. One minute later, it was taken out to place it into a drier at 100° C. for 5 minutes. Then, it was taken out from the drier. Then, the portion of the capacitor element, where it was immersed into the calcium phenolsulfonate aqueous solution, was immersed into a 35% 3,4-ethylenedioxythiophene ethanol solution which was prepared in advance, in such a manner that it is immersed at the depth of the portion where the polyimide solution was applied. It was taken out one minute later. Then, the capacitor element was immersed into a 45% ammonium persulfate aqueous solution for ten seconds, and then it was taken out and dried for 40 minutes at room temperature in order to polymerize to form a conductive polymer layer. Then, the capacitor element, a part of which surface is coated with a conductive polymer layer, was immersed into pure water for 30 minutes. It was then taken out to be dried at 70° C. for 30 minutes.

A series of processes from the step of immersing the capacitor element into the calcium phenolsulfonate aqueous solution to the step of drying it at 70° C. for 30 minutes was repeated eight times. Then, the capacitor element was dried at 150° C. for 60 minutes. Then, the conductive polymer layer was covered with a carbon paste and a silver paste such that a silver wire as a negative electrode was provided at a portion 3 mm distanced from the end of the lengthwise direction. Furthermore, the exterior was coated with an epoxy resin, and an aging process was performed so as to obtain an aluminum solid electrolyte capacitor.

Example 12

Instead of using the 0.5 mol/l calcium phenolsulfonate aqueous solution in Example 11, the 0.5 mol/l strontium phenolsulfonate aqueous solution (pH 6.0) prepared in accordance with Synthesis Example 2 was used. Other than that, the same procedure used in Example 11 was used to produce an aluminum solid electrolyte capacitor in this example.

Example 13

Instead of using the 0.5 mol/l calcium phenolsulfonate aqueous solution in Example 11, the 0.5 mol/l calcium cresolsulfonate aqueous solution (pH 6.0) prepared in accordance with Synthesis Example 4 was used. Other than that, the same procedure used in Example 11 was used to produce an aluminum solid electrolyte capacitor in this example.

Example 14

Instead of using the 45% ammonium persulfate aqueous solution, an oxidizer dopant solution was used. The oxidizer dopant solution in this Example was prepared as follows: 40% ammonium persulfate aqueous solution and 70% 2-methylimidazole phenolsulfonate aqueous solution were mixed together at a volume ratio of 1:1, into which lauryldimethylamineoxide was further added such that it was included at a concentration of 0.1%. Instead of repeating the polymerization process eight times, it was repeated five times in this example. Other than the differences, the same procedure used in Example 11 was used to produce an aluminum solid electrolyte capacitor in this example.

Comparative Example 7

Instead of using 0.5 mol/l calcium phenolsulfonate aqueous solution in Example 11, 0.5 mol/l sodium phenolsulfonate aqueous solution (pH 6.0) was used. Other than that, the same procedure used in Example 11 was used to produce an aluminum solid electrolyte capacitor in this example.

Comparative Example 8

Instead of using 0.5 mol/l calcium phenolsulfonate aqueous solution in Example 11, 0.5 mol/l ammonium phenolsulfonate aqueous solution (pH 6.0) was used. Other than that, the same procedure used in Example 11 was used to produce an aluminum solid electrolyte capacitor in this example.

Comparative Example 9

Instead of using 0.5 mol/l calcium phenolsulfonate aqueous solution in Example 11, 0.5 mol/l calcium m-xylenesulfonate aqueous solution (pH 6.0) was used. Other than that, the same procedure used in Example 11 was used to produce an aluminum solid electrolyte capacitor in this example.

Comparative Example 10

Instead of using 0.5 mol/l calcium phenolsulfonate aqueous solution in Example 11, 0.5 mol/l magnesium m-xylenesulfonate aqueous solution (pH 6.0) was used. Other than that, the same procedure used in Example 11 was used to produce an aluminum solid electrolyte capacitor in this example.

Comparative Example 11

Instead of using 0.5 mol/l calcium phenolsulfonate aqueous solution in Example 11, 0.5 mol/1 magnesium butylnaphthalenesulfonate aqueous solution (pH 6.0) was used. Other than that, the same procedure used in Example 11 was used to produce an aluminum solid electrolyte capacitor in this example.

Comparative Example 12

40% ferric p-toluenesulfonate butanol solution and 3,4-ethylenedioxythiophene were mixed together at a mass ratio of 4:1, and the mixture was strongly shaken for 10 seconds. Then, into the mixture, the same capacitor element used in Example 11 was quickly immersed, and 5 seconds later, it was taken out. The capacitor element was kept at room temperature for 30 minutes, and it was immersed in pure water for 30 minutes. Then, the capacitor element was taken out to be dried at 50° C. for 30 minutes.

A series of the processes from the step of immersing the capacitor element into the mixture of ferric p-toluenesulfonate butanol solution and 3,4-ethylenedioxythiophene to the step of drying it at 50° C. for 30 minutes was repeated five times so as to form a conductive polymer layer partially on the surface of the capacitor element. Then, the capacitor element was dried at 150° C. for 60 minutes. Then, the conductive polymer layer was coated with carbon paste and a silver paste, and a silver wire as a negative electrode was provided at a portion 3 mm distanced from the end of the lengthwise direction. The exterior was coated with an epoxy resin, and an aging process was performed so as to produce an aluminum solid electrolyte capacitor.

As to the aluminum solid electrolyte capacitor of Examples 11 to 14 and Comparative Examples 7 to 12, capacitance and ESR (equivalent series resistance) were measured. The results are shown in Table 2. The results in Table 2 were obtained as follows: each of capacitance and ESR was measured at 10 points, from which an averaged value was calculated while rounding off the decimal points.

Capacitance: Capacitance was measured by using LCR tester manufactured by HEWLETT PACKARD Company (4284A) at a condition of 25° C. and 120 Hz.

ESR: ESR was measured by using LCR tester manufactured by HEWLETT PACKARD Company (4284A) at a condition of 25° C. and 100 kHz.

TABLE 2

|  | Capacitance (µF) | ESR (mΩ) |
| --- | --- | --- |
| Example 11 | 9.8 | 14 |
| Example 12 | 9.9 | 13 |
| Example 13 | 9.8 | 13 |
| Example 14 | 9.9 | 12 |
| Comparative Example 7 | (*2) | (*2) |
| Comparative Example 8 | (*2) | (*2) |
| Comparative Example 9 | (*2) | (*2) |
| Comparative Example 10 | (*2) | (*2) |
| Comparative Example 11 | (*2) | (*2) |
| Comparative Example 12 | 9.8 | 14 |

Note that in Table 2, the mark (*2) indicates that the conductive polymer layer could not coat the whole of the portion where the conductive polymer layer should have been formed, and capacitance and ESR were not measured.

Five samples were arbitrarily selected from good samples of the aluminum solid electrolyte capacitors of Examples 11 to 14 and Comparative Example 12. They were kept at 125° C. for 500 hours, and then, capacitance and ESR were measured in the same manner as described above. The results are listed in Table 3 below. The results in Table 3 were obtained as follows: each of capacitance and ESR was measured at 5 points, from which an averaged value was calculated while rounding off the decimal points.

TABLE 3

|  | Capacitance (µF) | ESR (mΩ) |
| --- | --- | --- |
| Example 11 | 9.6 | 15 |
| Example 12 | 9.8 | 14 |
| Example 13 | 9.6 | 14 |
| Example 14 | 9.7 | 13 |
| Comparative Example 12 | 9.6 | 49 |

Furthermore, another sets of five samples were arbitrarily selected from good samples of the aluminum solid electrolyte capacitors of Examples 11 to 14 and Comparative Example 12. They were kept at an environment of 85° C. and 85% RH for 1000 hours, and then capacitance and ESR were measured in the same manner as described above. The results are listed in Table 4 below. The results in Table 4 were obtained as follows: each of capacitance and ESR was measured at 5 points, from which an averaged value was calculated with rounding off the decimal points.

TABLE 4

|  | Capacitance (µF) | ESR (mΩ) |
| --- | --- | --- |
| Example 11 | 9.9 | 14 |
| Example 12 | 9.8 | 14 |
| Example 13 | 9.8 | 14 |
| Example 14 | 9.8 | 13 |
| Comparative Example 12 | 9.7 | 24 |

As shown in Table 2, in the aluminum solid electrolyte capacitor of Comparative Examples 7 to 11, the conductive polymer layer did not cover the entire portion where the conductive polymer layer should have been formed. On the other hand, in the aluminum solid electrolyte capacitor of Examples 11 to 14, the reaction accelerator containing a salt of an anion derived phenolsulfonic acid or cresolsulfonic acid and a divalent or more cation other than a transition metal was used. Accordingly, the polymerization reaction of 3,4-ethylenedioxythiophene, a monomer, was promoted. Therefore, the conductive polymer layer could be evenly formed on the entire portion where the conductive polymer layer should have been formed, so as to produce good aluminum electrolyte capacitors. Also, the results in Tables 3 and 4 show that aluminum solid electrolyte capacitor in Examples 11 to 14 were excellent in the heat-resistance and the humidity resistance compared with that in Comparative Example 12.

Furthermore, note that during formation of the conductive polymer layer in Example 14, the ammonium persulfate aqueous solution as an oxidizer was substituted with an oxidizer dopant solution. The aluminum of solid electrolyte capacitor of Example 14, in spite of reducing the number of repeating times of the polymerization process, was excellent in the value of ESR compared with that of Example 11. The results show that even few number of repeating times of the polymerization process can form an aluminum solid electrolyte capacitor good in its properties.

Evaluation in Tantalum Solid Electrolyte Capacitor

Example 15

Tantalum sintered material is immersed in 0.1% phosphoric acid aqueous solution, while a voltage of 20V was applied to carry out a chemical conversion treatment to form a dielectric coating. Then, into 0.5% calcium phenolsulfonate aqueous solution prepared in accordance with Synthesis Example 1, the tantalum sintered material was immersed for 1 minute, and then it was taken out to dry it at 100° C. for 5 minutes. Then, into 35% 3,4-ethylenedioxythiophene ethanol solution, the tantalum sintered material was immersed for 1 minute, and then it was taken out to keep it at room temperature for 5 minutes. Then, into 35% ammonium persulfate aqueous solution, the tantalum sintered material was immersed for 5 seconds, and then it was taken out to keep it at room temperature for 30 minutes to form a conductive polymer layer. Then, the tantalum sintered material having its surface covered with conductive polymer layer was immersed into pure water for 30 minutes, and then it was taken out to dry it at 70° C. for 30 minutes.

A series of processes from the step of immersing the tantalum sintered material into the calcium phenolsulfonate aqueous solution to the step of drying it at 70° C. for 30 minutes was repeated sixteen times. Then, the conductive polymer layer was covered with a carbon paste and a silver paste to prepare a tantalum solid electrolyte capacitor.

Example 16

Instead of using 0.5 mol/l calcium phenolsulfonate aqueous solution in Example 15, 0.5 mol/l strontium phenolsulfonate aqueous solution (pH 6.0) prepared in accordance with Synthesis Example 2 was used. Other than that, the same procedure used in Example 15 was used to produce a tantalum solid electrolyte capacitor in this example.

Example 17

Instead of using 0.5 mol/l calcium phenolsulfonate aqueous solution in Example 15, 0.5 mol/l barium phenolsulfonate aqueous solution (pH 6.0) prepared in accordance with Synthesis Example 3 was used. Other than that, the same procedure used in Example 15 was used to produce a tantalum solid electrolyte capacitor in this example.

Example 18

Instead of using 0.5 mol/l calcium phenolsulfonate aqueous solution in Example 15, 0.5 mol/l calcium cresolsulfonate aqueous solution (pH 6.0) prepared in accordance with Synthesis Example 4 was used. Other than that, the same procedure used in Example 15 was used to produce a tantalum solid electrolyte capacitor in this example.

Example 19

Instead of using 0.5 mol/l calcium phenolsulfonate aqueous solution in Example 15, 0.5 mol/l ethylenediamine phenolsulfonate aqueous solution (pH 5.0) prepared in accordance with Synthesis Example 5 was used and the temperature of the solution was kept at 60° C. Other than that, the same procedure used in Example 15 was used to produce a tantalum solid electrolyte capacitor in this example.

Example 20

Instead of using 0.5 mol/l calcium phenolsulfonate aqueous solution, a solution (pH 5.0), in which 0.5 mol/l of ethylenediamine phenolsulfonate was dissolved into 20% ethylenediamine polystyrene phenolsulfonate aqueous solution as prepared in Synthesis Example 6, was used and the aqueous solution was kept at 60° C. Other than that, the same procedure used in Example 15 was used to produce a tantalum solid electrolyte capacitor in this example.

Example 21

Instead of using the 0.5 mol/l calcium phenolsulfonate aqueous solution, a solution (pH 1.5 when diluted into a concentration of 5%), in which 0.5 mol/l of ethylenediamine phenolsulfonate was dissolved into 20% ethylenediamine polystyrene phenolsulfonate aqueous solution as prepared in Synthesis Example 7, was used and the aqueous solution was kept at 60° C. Other than that, the same procedure used in Example 15 was used to produce a tantalum solid electrolyte capacitor in this example.

Example 22

Instead of using 35% ammonium persulfate, an oxidizer dopant solution in which 40% ammonium persulfate was mixed with 70% 2-methylimidazole phenolsulfonate aqueous solution (pH 5.0) at a volume ratio of 1:1 was used, and the number of repeating the polymerization process was decreased from 16 times to 10 times. Other than that, the same procedure used in Example 15 was used to produce a tantalum solid electrolyte capacitor in this example.

Example 23

Instead of using 35% ammonium persulfate, an oxidizer dopant solution in which 40% ammonium persulfate was mixed with 70% 2-methylimidazole phenolsulfonate aqueous solution (pH 5.0) at a volume ratio of 1:1 with further addition of decyldimethylamineoxide at a concentration of 0.2% was used, and the number of repeating the polymerization process was decreased from 16 times to 10 times. Other than that, the same procedure used in Example 15 was used to produce a tantalum solid electrolyte capacitor in this example.

Example 24

Instead of using 35% ammonium persulfate, an oxidizer dopant solution in which 40% ammonium persulfate was mixed with 70% 4-methylimidazole phenolsulfonate aqueous solution (pH 5.0) at a volume ratio of 1:1 with further addition of decyldimethylamineoxide at a concentration of 0.2% was used, and the number of repeating the polymerization process was decreased from 16 times to 10 times. Other than that, the same procedure used in Example 15 was used to produce a tantalum solid electrolyte capacitor in this example.

Example 25

A tantalum sintered material was prepared in the same manner as Example 15 so as to form a dielectric coating. Then, it was immersed into 35% 3,4-ethylenedioxythiophene ethanol solution for 1 minute, and then it was taken out to keep it at room temperature for 5 minutes. Then, into the same oxidizer dopant solution used in Example 23, the tantalum sintered material was immersed for 5 seconds, and then taken out to keep it for 5 minutes. Then, into the 0.5% calcium phenolsulfonate aqueous solution (pH 6.0) prepared in accordance with Synthesis Example 1, the tantalum sintered material was immersed for 5 seconds, and then it was taken out to dry it at room temperature for 30 minutes to form a conductive polymer layer. Then, the tantalum sintered material having its surface covered with conductive polymer layer was immersed into pure water for 30 minutes, and then it was taken out to dry it at 70° C. for 30 minutes.

A series of processes from the step of immersing the tantalum sintered material into the 3,4-ethylenedioxythiophene ethanol solution to the step of drying it at 70° C. for 30 minutes was repeated ten times. Then, the conductive polymer layer was covered with a carbon paste and a silver paste to prepare a tantalum solid electrolyte capacitor.

Example 26

Instead of using 35% ammonium persulfate, an oxidizer dopant solution in which 40% ammonium persulfate was mixed with 70% 2-methylimidazole phenolsulfonate aqueous solution (pH 5.0) at a volume ratio of 1:1 was used, and the number of repeating the polymerization process was reduced from 16 times to 10 times. Other than that, the same procedure used in Example 19 was used to produce a tantalum solid electrolyte capacitor in this example.

Example 27

Instead of using 35% ammonium persulfate, an oxidizer dopant solution in which 40% ammonium persulfate was mixed with 70% 2-methylimidazole phenolsulfonate aqueous solution (pH 5.0) at a volume ratio of 1:1 was used, and the number of repeating the polymerization process was reduced from 16 times to 10 times. Other than that, the same procedure used in Example 20 was used to produce a tantalum solid electrolyte capacitor in this example.

Example 28

Instead of using 35% ammonium persulfate, an oxidizer dopant solution in which 40% ammonium persulfate was mixed with 70% 2-methylimidazole phenolsulfonate aqueous solution (pH 5.0) at a volume ratio of 1:1 was used, and the number of repeating the polymerization process was reduced from 16 times to 10 times. Other than that, the same procedure used in Example 21 was used to produce a tantalum solid electrolyte capacitor in this example.

Comparative Example 13

Instead of using 0.5 mol/l calcium phenolsulfonate aqueous solution in Example 15, 0.5 mol/l sodium phenolsulfonate aqueous solution (pH 6.0) was used. Other than that, the same procedure used in Example 15 was used to produce a tantalum solid electrolyte capacitor in this example.

Comparative Example 14

Instead of using 0.5 mol/l calcium phenolsulfonate aqueous solution in Example 15, 0.5 mol/l ammonium phenolsulfonate aqueous solution (pH 6.0) was used. Other than that, the same procedure used in Example 15 was used to produce a tantalum solid electrolyte capacitor in this example.

Comparative Example 15

Instead of using 0.5 mol/l calcium phenolsulfonate aqueous solution in Example 15, 0.5 mol/l calcium m-xylenesulfonate aqueous solution (pH 6.0) was used. Other than that, the same procedure used in Example 15 was used to produce a tantalum solid electrolyte capacitor in this example.

Comparative Example 16

Instead of using 0.5 mol/l calcium phenolsulfonate aqueous solution in Example 15, 0.5 mol/l magnesium m-xylenesulfonate aqueous solution (pH 6.0) was used. Other than that, the same procedure used in Example 15 was used to produce a tantalum solid electrolyte capacitor in this example.

Comparative Example 17

40% butanol solution of ferric p-toluenesulfonate was mixed with 3,4-ethylenedioxythiophene at a mass ratio of 4:1, and the mixture was strongly shaken for 10 seconds. Into this mixture, the same tantalum sintered material (that is, the tantalum sintered material having formed a dielectric coating) as used in Example 15 was immersed quickly for 5 seconds, which was then taken out. The tantalum sintered material was kept for 30 minutes at room temperature and then it was immersed in pure water for 30 minutes. Then, the tantalum sintered material was taken out and dried for 30 minutes at 50° C.

The sequential process from the step of immersing the tantalum sintered material into the mixture of the ferric p-toluenesulfonate butanol solution and 3,4-ethylenedioxythiophene to the step of drying at 50° C. for 30 minutes was repeated five times to form a conductive polymer layer on the surface of the tantalum sintered material. Then, the conductive polymer layer was covered with a carbon paste and a silver paste to prepare a tantalum solid electrolyte capacitor.

As to the tantalum solid electrolyte capacitor of Examples 15 to 28 and Comparative Examples 13 to 17, the capacitance and ESR were measured in the same manner as described in connection with the aluminum solid electrolyte capacitor. The results are listed in Table 5 below. The results in Table 5 were obtained as follows: each of capacitance and ESR was measured at 10 points, from which an averaged value was calculated while rounding off the decimal points.

TABLE 5

|  | Capacitance (μF) | ESR (mΩ) |
|---|---|---|
| Example 15 | 110 | 34 |
| Example 16 | 109 | 35 |
| Example 17 | 106 | 36 |

TABLE 5-continued

|  | Capacitance (µF) | ESR (mΩ) |
|---|---|---|
| Example 18 | 104 | 35 |
| Example 19 | 103 | 39 |
| Example 20 | 105 | 38 |
| Example 21 | 103 | 37 |
| Example 22 | 105 | 35 |
| Example 23 | 110 | 33 |
| Example 24 | 110 | 33 |
| Example 25 | 108 | 33 |
| Example 26 | 111 | 34 |
| Example 27 | 109 | 34 |
| Example 28 | 108 | 32 |
| Comparative Example 13 | (*3) | (*3) |
| Comparative Example 14 | (*3) | (*3) |
| Comparative Example 15 | (*3) | (*3) |
| Comparative Example 16 | (*3) | (*3) |
| Comparative Example 17 | 108 | 34 |

Note that in Table 5, the mark (*3) indicates that the conductive polymer layer could not coat the whole of the surface of the tantalum sintered material so that the capacitance and the ESR were not measured.

Five samples were arbitrarily selected from good samples of the tantalum solid electrolyte capacitor of Examples 15 to 28 and Comparative Example 17. They were kept at 125° C. for 500 hours, and then, capacitance and ESR were measured in the same manner as described above. The results are listed in Table 6 below. The results in Table 6 were obtained as follows: each of capacitance and ESR was measured at 5 points, from which an averaged value was calculated with rounding off the decimal points.

TABLE 6

|  | Capacitance (µF) | ESR (mΩ) |
|---|---|---|
| Example 15 | 106 | 37 |
| Example 16 | 105 | 38 |
| Example 17 | 103 | 40 |
| Example 18 | 100 | 40 |
| Example 19 | 100 | 42 |
| Example 20 | 102 | 42 |
| Example 21 | 100 | 40 |
| Example 22 | 102 | 38 |
| Example 23 | 107 | 36 |
| Example 24 | 106 | 36 |
| Example 25 | 105 | 36 |
| Example 26 | 106 | 37 |
| Example 27 | 105 | 38 |
| Example 28 | 103 | 35 |
| Comparative Example 17 | 103 | 75 |

Furthermore, another sets of five samples were arbitrarily selected from good samples of the tantalum solid electrolyte capacitors of Examples 15 to 28 and Comparative Example 17. They were kept at an environment of 85° C. and 85% RH for 1000 hours, and then capacitance and ESR were measured in the same manner as described above. The results are listed in Table 7 below. The results in Table 7 were obtained as follows: each of capacitance and ESR was measured at 5 points, from which an averaged value was calculated with rounding off the decimal points.

TABLE 7

|  | Capacitance (µF) | ESR (mΩ) |
|---|---|---|
| Example 15 | 108 | 36 |
| Example 16 | 107 | 36 |
| Example 17 | 105 | 38 |

TABLE 7-continued

|  | Capacitance (µF) | ESR (mΩ) |
|---|---|---|
| Example 18 | 103 | 38 |
| Example 19 | 107 | 40 |
| Example 20 | 107 | 40 |
| Example 21 | 105 | 39 |
| Example 22 | 104 | 37 |
| Example 23 | 109 | 35 |
| Example 24 | 109 | 35 |
| Example 25 | 106 | 35 |
| Example 26 | 107 | 35 |
| Example 27 | 107 | 35 |
| Example 28 | 105 | 33 |
| Comparative Example 17 | 107 | 65 |

As shown in Table 5, in the tantalum solid electrolyte capacitor of Comparative Examples 13 to 16, the surface of the tantalum sintered material of the element was not covered with the conductive polymer layer. On the other hand, in the tantalum solid electrolyte capacitor of Examples 15 to 28, the reaction accelerator containing a salt of an anion derived from phenolsulfonic acid or cresolsulfonic acid and a divalent or more cation other than a transition metal was used. Accordingly, the polymerization reaction of 3,4-ethylenedioxythiophene, a monomer, was promoted. Therefore, the surface of the tantalum sintered material of the element could be evenly covered with the conductive polymer layer, so as to produce good tantalum electrolyte capacitors.

Moreover, the results in Example 15 and 22 to 24 using the same reaction accelerator, that is, calcium phenolsulfonate, are compared as follow: In Examples 22 to 24, instead of using an ammonium persulfate solution as an oxidizer solution, an oxidizer dopant solution including a conductive polymer polymerization dopant such as 2-methylimidazole phenolsulfonate and 4-methylimidazole phenolsulfonate was used. The conductive polymers in Examples 22-24 formed good tantalum solid electrolyte capacitor, compared with Example 15 in which the oxidizer solution did not include the dopant, in spite of few number of repeating the polymerization process. The effects by using the reaction accelerator together with the oxidizer dopant solution including a dopant were shown in these examples.

Similarly, a comparison was made between the results of Examples 26 and 19 (both using ethylenediamine phenolsulfonate as a reaction accelerator); the results of Examples 27 and 20 (both using a solution (pH 5) in which ethylenediamine phenolsulfonate was dissolved into 20% ethylenediamine polystyrene phenolsulfonate aqueous solution as a reaction accelerator); and the results of Examples 28 and 21 (using a solution (pH 1.5 when diluted into a concentration of 5%) in which ethylenediamine phenolsulfonate was dissolved into 20% ethylenediamine polystyrene phenolsulfonate aqueous solution). The number of repeating polymerization in Example 26 was fewer than that in Example 19; the number of repeating polymerization in Example 27 was fewer than that in Example 20; and the number of repeating polymerization in Example 28 was fewer than those in Example 21. Nonetheless, the conductive polymers in Examples 26-28 formed good tantalum solid electrolyte capacitor. Accordingly, the results show the effects in using the reaction accelerator in addition to the oxidizer dopant solution. Also, the results in Tables 6 and 7 show that the tantalum solid electrolyte capacitors in accordance with Examples 15 to 28 were better in heat-resistance and humidity-resistance than that in Comparative Example 17.

INDUSTRIAL APPLICABILITY

As explained above, the present invention provides a reaction accelerator which can promote the polymerization reaction of the monomer in producing a conductive polymer having a high electric conductivity. Also, according to the present invention, the use of the reaction accelerator can produce a conductive polymer having a high electric conductivity as well as heat-resistance. The use of the conductive polymer as a solid electrolyte can produce a solid electrolyte capacitor reliable over a long period of time.

What is claimed is:

1. A method of using a salt serving as a reaction accelerator during polymerizing conductive polymer, the method comprising:
providing the salt, wherein the salt consists of an anion derived from a sulfonic acid having a skeleton of benzene or naphthalene, the anion having at least one OH group, and at least one divalent or more cation other than a transition metal cation,
contacting a monomer to the salt, and
polymerizing the monomer while using the salt as the reaction accelerator.

2. The method according to claim 1, wherein the salt is in an aqueous solution.

3. The method according to claim 1, wherein the reaction accelerator is in an aqueous solution having a concentration of 5 mass % has a pH of 1 or more.

4. The method according to claim 1, wherein the anion is one selected from the group consisting of phenol sulfonic acid or cresol sulfonic acid.

5. The method according to claim 1, wherein said divalent or more cation is selected from the group consisting of calcium ion, strontium ion, barium ion, aluminum ion and ethylenediamine ion.

6. The method according to claim 1, wherein the monomer is polymerized in a chemical oxidation polymerization.

* * * * *